United States Patent [19]
Volz et al.

[11] Patent Number: 5,755,743
[45] Date of Patent: May 26, 1998

[54] IMPLANTABLE UNIT

[75] Inventors: Andreas Volz, München; Hans Leysieffer, Taufkirchen, both of Germany

[73] Assignee: IMPLEX GmbH Spezialhorgerate, Ismaning, Germany

[21] Appl. No.: 733,140

[22] Filed: Oct. 16, 1996

[30] Foreign Application Priority Data

Jun. 5, 1996 [DE] Germany .................. 196 22 669.4

[51] Int. Cl.$^6$ .................................................. A61N 1/375
[52] U.S. Cl. .................................................. 607/37; 607/36
[58] Field of Search .................................. 607/36, 37

[56] References Cited

U.S. PATENT DOCUMENTS

| 4,262,673 | 4/1981 | Kinney et al. . |
| 4,605,007 | 8/1986 | Heraly . |

FOREIGN PATENT DOCUMENTS

| 0 006 281 | 7/1978 | European Pat. Off. . |
| 0 001 897 | 5/1979 | European Pat. Off. . |
| 0 052 690 A1 | 6/1982 | European Pat. Off. . |
| 0 052 879 A1 | 6/1982 | European Pat. Off. . |
| 0 052 879 B1 | 9/1985 | European Pat. Off. . |
| 0 306 443 | 3/1989 | European Pat. Off. . |
| 0 339 877 | 11/1989 | European Pat. Off. . |
| 0 357 941 | 3/1990 | European Pat. Off. . |
| 0 442 807 A1 | 8/1991 | European Pat. Off. . |
| 0 587 379 A2 | 3/1994 | European Pat. Off. . |
| 34 00 191 A1 | 8/1984 | Germany . |
| 33 31 620 A1 | 3/1994 | Germany . |
| WO89/05170 | 6/1989 | WIPO . |
| WO90/02581 | 3/1990 | WIPO . |
| WO91/04069 | 4/1991 | WIPO . |
| WO91/16947 | 11/1991 | WIPO . |
| WO93/02742 | 2/1993 | WIPO . |
| WO93/05844 | 4/1993 | WIPO . |

*Primary Examiner*—Scott M. Getzow
*Attorney, Agent, or Firm*—Sixbey, Friedman, Leedom & Ferguson; David S. Safran

[57] ABSTRACT

An implantable unit with at least one contact arrangement for connection of an electrical or electronic device (11), which is hermetically sealed within a housing (10), to at least one cable set (12, 14) that is routed out of the housing. The contact arrangement has a first contact (22), a second contact (30) supported on an elastic body (16), a closing mechanism (18, 19, 20) for engaging the front of the first contact to the front of the second contact and at least one sealing land (28) which surrounds the first contact, which is pressed into the elastic body when the contacts engage, and which seals the contacts relative to the outside of the unit.

17 Claims, 5 Drawing Sheets

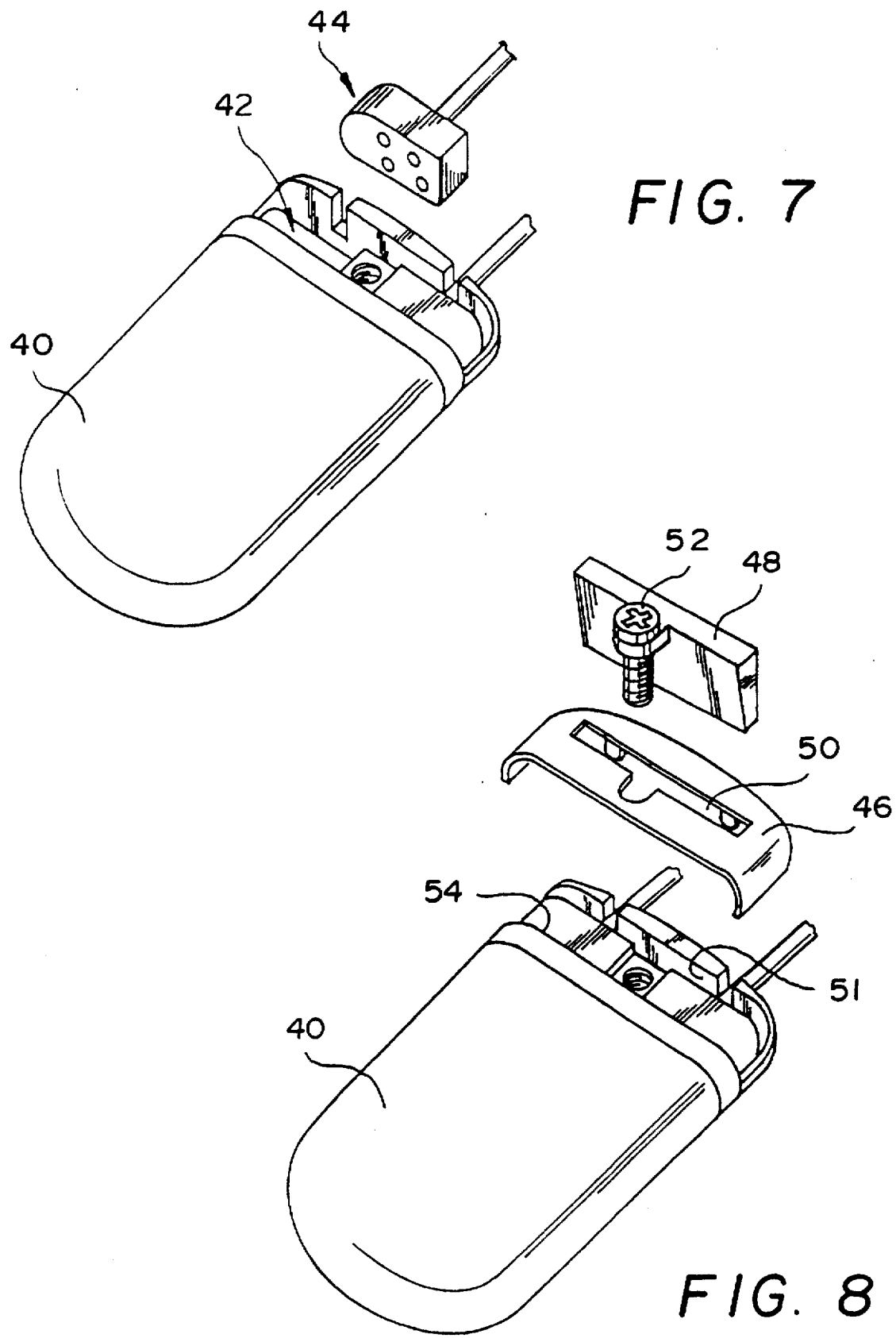

IMPLANTABLE UNIT

BACKGROUND OF THE INVENTION

1. Field of the Invention

The invention relates to an implantable unit with at least one contact arrangement for connection of an electrical or electronic device, which is hermetically sealed in a housing, to at least one cable set routed out of the housing. In particular, the invention relates to a detachable electrical connection between an implant housing which accommodates active electronic components and sensors or actuators which can be placed at an entirely defined location in the body and which are operated by the active electronic components.

2. Description of Related Art

Implantable plug-and-socket connections are used in cardiac pacemakers, defibrillators and cardioverters. When the implanted electronics are replaced, which becomes necessary due to the power source being drained, the sensors and actuators, which require complex surgical techniques when being implanted or explanted, are left on site, if possible. In cardiac pacemakers, this has led to a standard, so that different models can be connected to the sensors and actuators once they are in place. The requirements for the electrode plug and the socket are set forth in DIN VDE 0750 Part 91 which also contains an exact stipulation of the dimensions and tolerances. Plugs designed according to this DIN standard work like a banana plug, but have two contact surfaces with different diameters which are separated from one another by sealing O-rings (sealing lips). The dimensions of the plug receiver are likewise established according to the plug in this DIN standard. The diameters of the sealing lips and the plug receiver determine the contact pressure and the sealing action against penetrating bodily fluid which can be achieved with it. The standard furthermore contains test specifications relating to the insulation impedance which must be greater than 50 k$\Omega$.

Numerous patents relate to production engineering of the plug receiver on a hermetically sealed housing, the production engineering of the plug, the type of contact making, and fixing of the plug in the plug housing. All the following patents have in common a cylindrical opening for holding a cylindrical plug with one or more contact points and insulating sealing lips:

European Applications 0 052 690; EP-A-0 006 281; EP-B-0 052 879; EP-A-0 442 807 and EP-A-0 357 941; U.S. Pat. No. 4,262,673; and International Applications WO-A-90/02581; WO-A-91/04069; WO-A-91/16947; WO-A-93/05844; WO-A-93/02742; and WO-A-89/05170.

European Applications EP-A-0 587 379 and EP-A-0 306 443 relate to a coaxial embodiment of the described plug-and-socket connection system.

European Application EP-A-0 339 877 calls for making contact with the cylindrical plug using conductive silicone in the plug receiver. By alternating conductive and nonconductive layers, several contacts can be made on the cylindrical plug. Since both the contacts as well as the insulators are flexible, the formation of sealing lips can be abandoned by corresponding contact pressure, both in the contact zone and also in the insulating zone, by matching the diameters of the plug receiver and of the pin. The contact pressure is limited by the slide path which must be traversed when the plug is inserted.

German Patent Application DE-A-33 31 620 differs from the cylindrical plug which can contain several contact surfaces which are insulated from one another by sealing lips, and calls for several contact pins which project vertically from a plug base plate. O-rings placed around the contacts provide for the seal when the plug base plate is screwed against the housing. By using screws to produce the sealing action, a much higher contact pressure can be achieved, since this pressure need not be overcome when the plug, is manually inserted. The inventor specifies a gas-tight seal. This document represents the closest prior art for the invention described below which, likewise, imposes higher demands on the insulation between the contacts.

European Application EP-A-0 001 897 describes the possibility of an electrical connection between two substrates using alternating layers of nonconductive and conductive silicones. It is assumed that the substrates are located directly in the bodily medium.

Implants of the initially mentioned type, for example, implantable hearing aids, cardiac pacemakers, drug pumps, etc. should take up as little space as possible upon implantation in the body and thus they should be largely miniaturized. If in the course of this miniaturization the plug-and-socket connections known from the prior art are likewise miniaturized, plug,-and-socket connections are obtained with very thin, elongated contacts which can be easily broken off, bent or otherwise damaged when inserted into the corresponding socket.

SUMMARY OF THE INVENTION

Therefore, a primary object of the present invention is to devise an implantable unit of the initially mentioned type, in which, on the one hand, a high degree of miniaturization can be achieved without using overly sensitive components, and in which, on the other hand, provisions are made for safe and reliable contact between the device accommodated in the housing and the cable set(s).

This object is achieved according to preferred embodiments of the invention by the fact that, in an implantable unit of the initially mentioned type, the contact arrangement has a first contact, a second contact supported on an elastic body, a closing mechanism for engaging the front of the first contact to the front of the second contact, and at least one sealing land which surrounds the first contact, which is pressed into the elastic body when the contacts engage, and seals the contacts relative to the outside.

In this way, an electronic contact principle is obtained which has no socket and no plug to be inserted into the socket. By using two contact elements which are pressed against one another on the front and which can be made more or less flat, a high degree of miniaturization is possible, since the danger of breaking or bending of thin plug pins can be precluded and the necessary depth for the plug path is eliminated. Both the contact force as well as the force which is necessary to seal the contacts against penetrating bodily fluid are produced via the same closing mechanism. By choosing a correspondingly high pressure, on the one hand, a reliable, gas-tight connection which is functionally equivalent to a weld connection is formed at the point of contact between the contacts. On the other hand, the contacts are hermetically sealed, for example, against the penetration of body fluid.

In order to further improve the sealing action, a plurality of sealing lands which are concentric to one another can be provided, for which, when using a plurality of contact arrangements, for each contact arrangement, there can be at least one sealing land which is assigned to this contact arrangement.

If the first contact is fixed to the housing and is joined to the electrical or electronic device which is accommodated in the housing, while the second contact is connected to the cable set, the first contact can be formed directly by a feedthrough of the electrical or electronic device through the housing; in this case, preferably, an electrically insulating molding is provided which surrounds the feedthrough.

According to one embodiment of the invention, the closing mechanism has a sealing cap which is connected to at least one cable set, and in which there is at least a first contact and/or at least a second contact, the engagement arrangement being provided in order to keep the sealing cap engaged to the housing. In this case, the sealing cap with the contacts located therein forms a unit which can be attached, for example, via a thread assigned to the housing and a screw assigned to the sealing cap on the housing. Alternatively, there can be a catch connection which acts between the sealing cap and the housing.

If replacement of only the cable set is to be possible, it is advantageous if the cable set is provided with a terminal fitting which bears one or more first or second contacts, and if the closing mechanism has a sealing cap with a receiver for the terminal fitting. The possibility of replacing the cable set is especially advantageous when several cable sets are to be connected to the device accommodated in the housing. In this embodiment, a screw and a threaded receptacle for it, or a catch connection, are also used to keep the sealing cap engaged to the housing.

If a screw is used for engagement between the sealing cap and the housing, the arrangement is such that, for contacting between the first and the second contacts, a specific torque which is applied to the screw is necessary. By using a suitable tool, especially a torque wrench, excess stress is avoided, both of the screw and also of the components which come into contact with one another, yet, the surgeon can still be certain that the desired contacts are established. Furthermore, the closing force can thus be reliably introduced even with a large number of seals and contacts to be closed.

Depending on the type of device to be implanted, it can be advantageous if the terminal fittings are inserted in a direction perpendicular to the cable sets, and if the force for connecting the contacts can be applied in a direction perpendicularly to the direction of the action of this force. For this reason, in another embodiment of the invention, on at least one cable set, there can be a terminal fitting and the housing can have a trough-shaped elongation to hold at least one terminal fitting. Furthermore, there can be a wedge for insertion between the wall side of the trough-shaped elongation, which is at a distance from the housing, and a terminal fitting which is inserted into the trough-shaped elongation. If the wedge is, for example, inserted and fixed by means of a screw provided especially for this purpose, it presses the terminal fitting in the direction perpendicular to the screw axis against the housing.

By this path-force transformation, the closing mechanism can be operated from above also for a housing which is implanted parallel to the surface of the patient's skin, as, for example, a housing embedded in the skull bone, so that, to replace or couple the cable set, the housing need not be removed from its fixed anchor, as, for example, a bone bed. Thus, the treating surgeon has both hands free for the connection process and he need not hold the housing for the connection process, as in conventional arrangements. The danger of applying tension during connection to the lines which are joined to the actuators or sensors, which can lead to damage of the lines, which are very thin if necessary (especially for multichannel systems), or of sensors and actuators, is thus largely prevented. In many conventional devices in which first the connection process must be completed before they are placed at the final implantation site, moreover, for the connection process, a certain length of excess cable is necessary which is placed at the implantation site in a loop around the housing. In contrast, the coupling principle proposed here enables direct and short line paths between the device accommodated in the housing and the sensor or actuator components which are connected thereto.

To fix the wedge in position, however, between it and the housing there can be a catch device, so that the wedge can be manually inserted and a tool for operating the screw can be dispensed with.

Preferred embodiments of the invention are detailed in the following with reference to the accompanying drawings.

BRIEF DESCRIPTION OF THE DRAWINGS

FIG. 7 is a perspective view of an implantable housing according to another embodiment; and FIG. 8 is an exploded perspective view of the implantable housing shown in FIG. 7 and the components used for fixing the contacts and for sealing the housing.

DETAILED DESCRIPTION OF THE PREFERRED EMBODIMENTS

Figure 1:
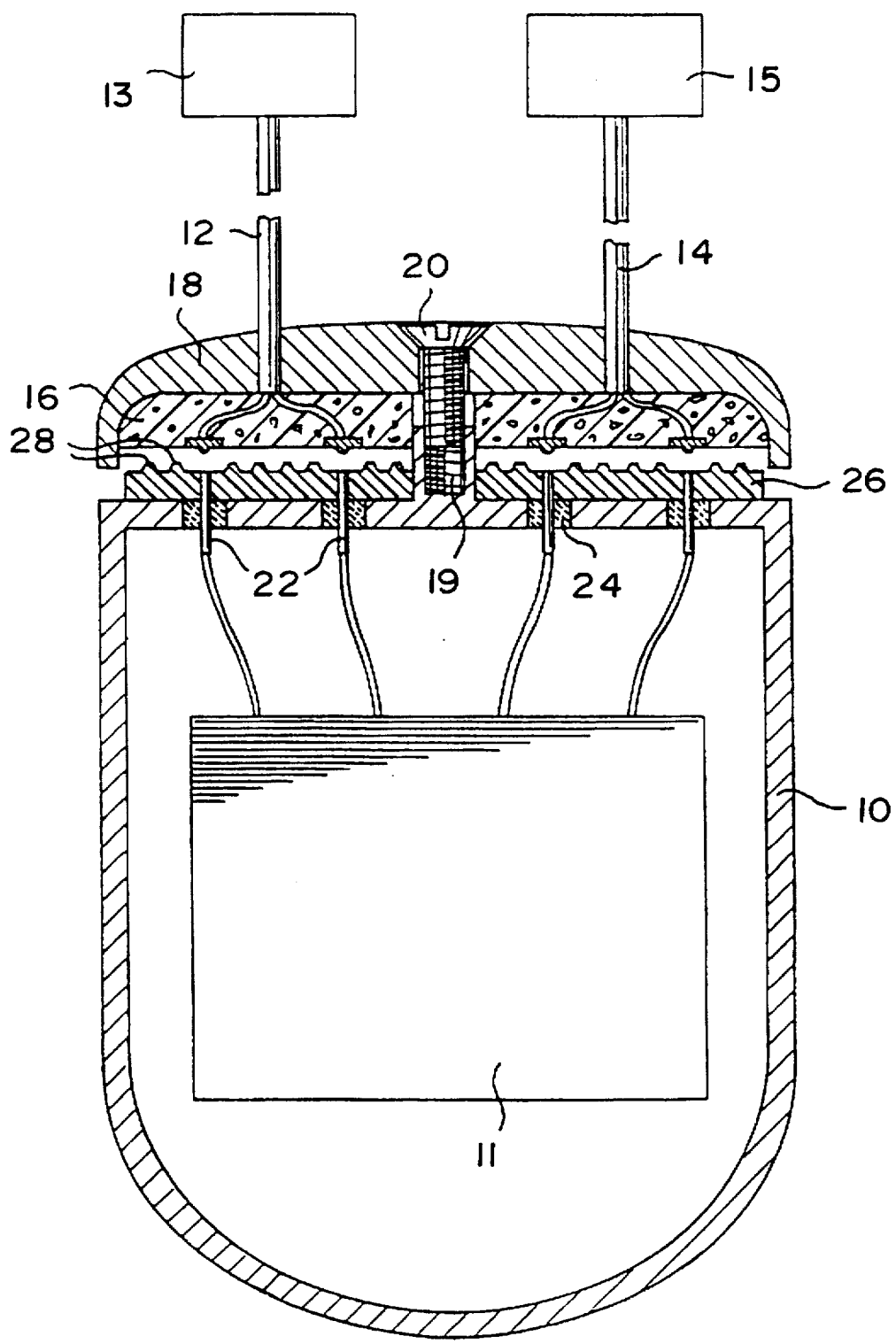
FIG. 1 shows a sectional view of an implantable housing.

FIG. 1 shows a section through an implantable unit having a hermetically sealed housing 10 for holding an electrical or electronic device 11, shown as a block, which can be, for example, the signal converter of an implantable hearing aid, the signal processing electronics of a cardiac pacemaker, etc. The connection of the device accommodated in hermetically sealed housing 10 with actuator or sensor components 13, 15, shown likewise only as blocks, is effected via cable sets 12, 14. The ends of cable sets 12, 14 are embedded in terminal fittings 16 which are inserted in an end cap 18 that is provided on the front of housing 10 when the unit is implanted. A screw connection is formed by a screw 20 which is carried by the sealing cap 18 and a threaded receptacle 19 carried by the housing 10 and is used to fix terminal fittings 16. FIG. 1 shows an embodiment for an implantable unit with a sensor and an actuator element 13, 15 which can be arranged separately from one another in space, and which, therefore, require their own cable set. However, it goes without saying that the principle described below can be implemented in the same way in embodiments with only one cable set or with more than two cable sets. If the sensor and actuator channels lead to different implantation sites, there should be one cable set per implantation site, the terminal fitting of which can be removed independently from the others, so that a fault in the sensors or actuators does not necessitate a complete new operation (RE-OP).

To form the housing-side contacts, on the front of housing 10, there are feedthroughs 22 with flat front side, which are separated by insulator 24, for example, ceramic, from the housing generally made of metal body, and which are held rigidly. Insulator 24, furthermore, provides a hermetic seal between the feedthroughs 22 and the housing 10. On the side of housing 10 which contains the wire-shaped feedthroughs 22, a molding 26 of electrically insulated inelastic material, for example, of a polycarbonate, is attached, with the front end surfaces of the feedthrough wires 22 lying flush with the front surface of the molding 26. To seal the contact surfaces of the front end surfaces of the feedthrough wires 22 against contact with body fluids, the molding 26 has one or more sealing lands 28 which project forwardly from its front surface. These sealing lands 28 are buried in the terminal fittings 16 (which are made of an elastic material) when the housing 10 and end cap 18 are screwed together.

Figure 2:
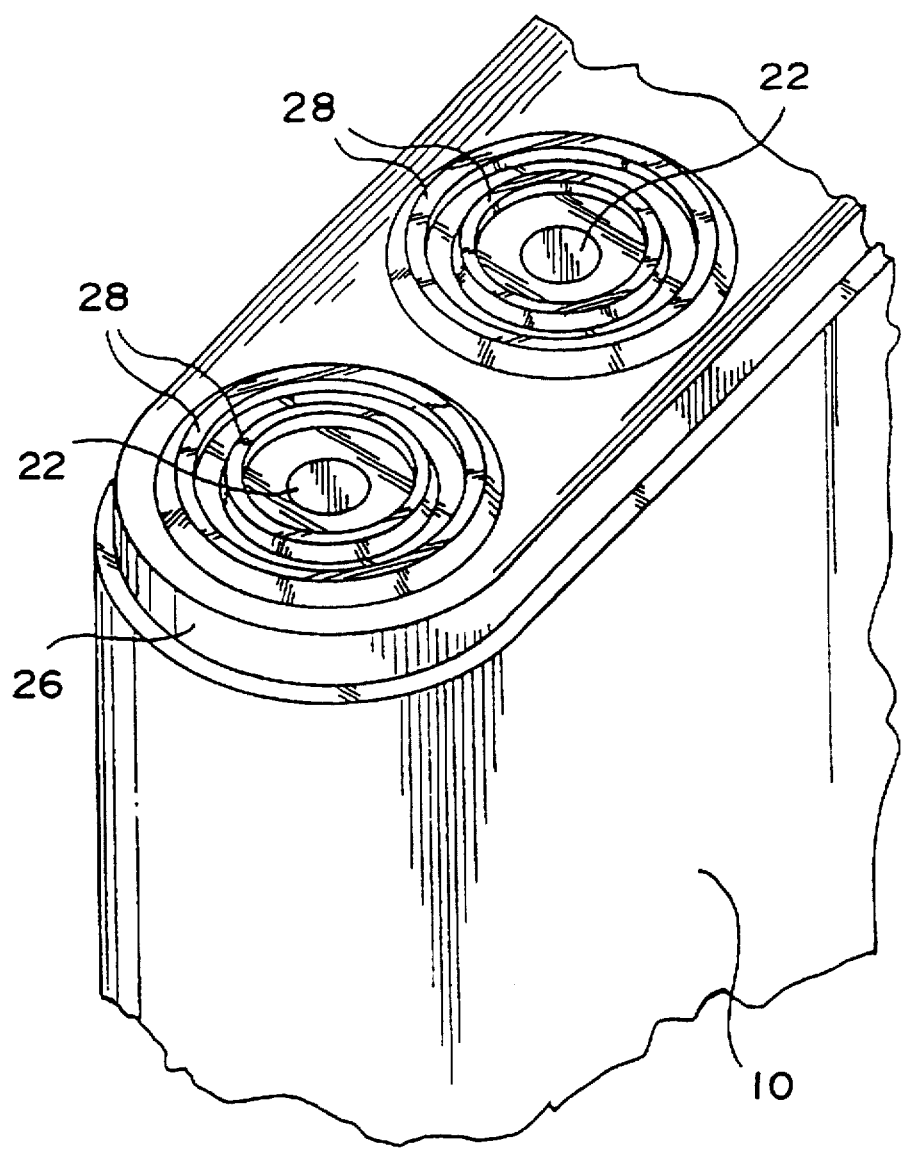
FIG. 2 shows a schematic perspective view of a portion of the front side of the housing shown in FIG. 1.

In the embodiment shown in FIG. 1, as is especially apparent from FIG. 2, two circular sealing lands 28 concentrically surround each of the feedthroughs 22. Instead or in addition, sealing lands can also be provided which surround several contacts, for example, the contacts assigned to one terminal fitting or even all contacts of the entire unit.

Figure 5:
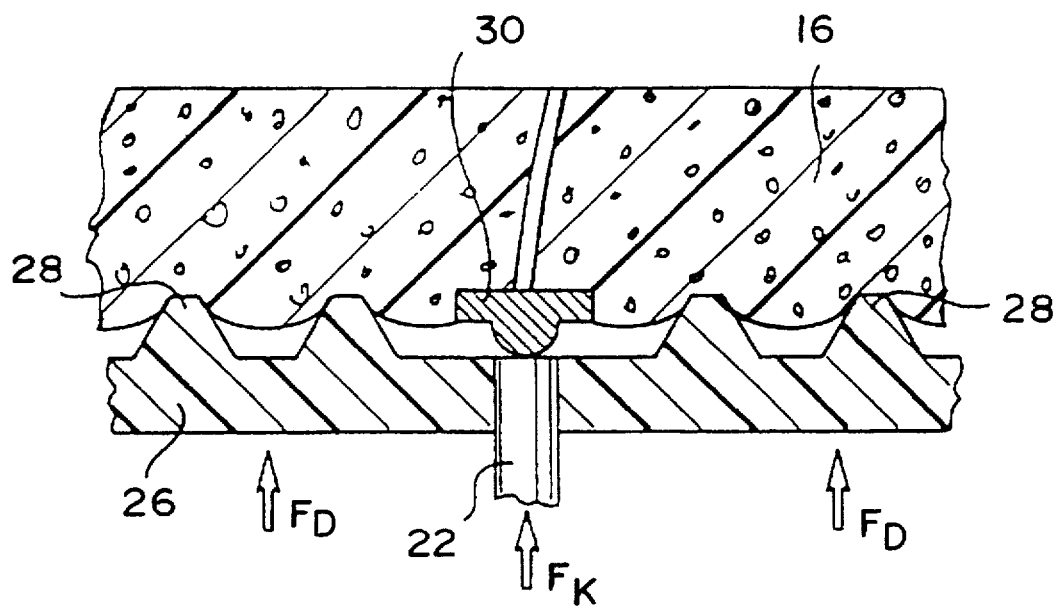
FIG. 5 shows an enlarged sectional view of a contact arrangement in the closed state.

The dimensions of the molding 26, the terminal fittings 16 and end cap 18 are selected such that the elastic material of terminal fittings 16, which is preferably silicone, is not stressed beyond its elastic limit when end cap 18 is screwed on, so that a resilient restoration force is preserved which produces a high pressure on the sealing lands and which is designated sealing force $F_D$ in FIG. 5. In this same way, when end cap 18 is screwed on, a spring-like contact force $F_K$ is produced between feedthroughs 22 and the cap-side contacts 30 which are embedded in the elastic material of the terminal fittings 16, by pushing contacts 30, when they meet the nonreceding contact surfaces of feedthroughs 22, into the elastic material of terminal fittings 16. Contact force $F_K$ is preferably selected to be so large that the surfaces of the metal contacts begin to flow and ensure a gas-tight seal of the point of contact.

Preferably, in the manner shown for contacts 30, one of two mutually engaging contacts has a rounded front side in order to obviate the necessity to maintain unnecessarily high precision with regard to parallelism for multiple planar contacts. The required contact force depends on the metallic material and the required contact surface (current carrying capacity). The elastic limit of the elastic material for a given bearing surface of the contact, which must be much greater than the actual contact surface, is a limiting factor.

Figure 3:
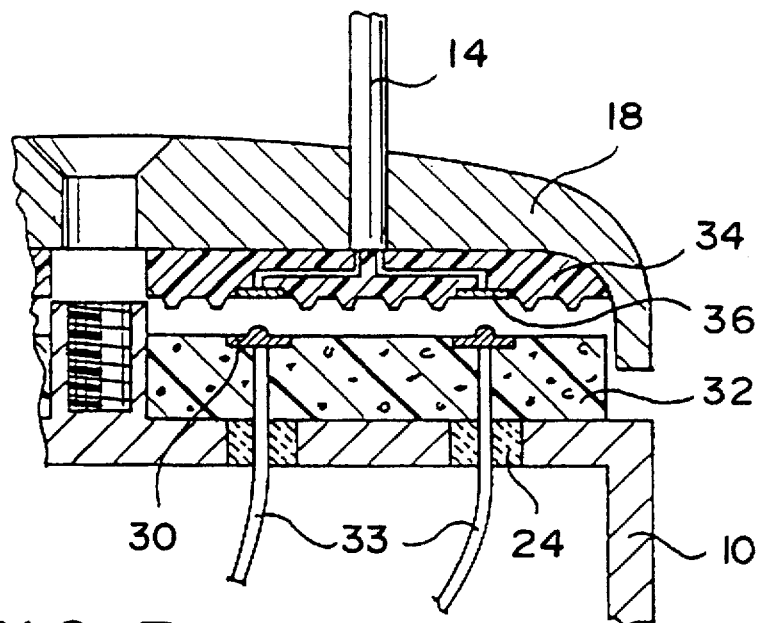
FIG. 3 is a sectional view showing part of an implantable housing similar to FIG. 1.

The spatial arrangement of the rigid molding provided with sealing lands and of the elastic body can be interchanged, if desired, as shown in FIG. 3 where, in this case, an elastic body 32 is applied to the front side of housing 10, for example, by means of cementing or glueing, and a rigid terminal fitting 34 analogous to molding 26 in FIGS. 1 and 2 is applied to end cap 18. The two contacts 30 are embedded in elastic body 32 and are provided with a front surface which is approximately hemispherically rounded. Contacts 30 are joined via connection wires 33 (which are electrically sealed relative to housing 10 by means of insulators 24) to the electrical or electronic device which is accommodated within the housing 10. According to this embodiment, the end of cable set 14 is connected to two disk-shaped contacts 36 that have a flat front surface and are embedded in the rigid terminal fitting 34 within the ring-shaped sealing lands.

In order to prevent confusion of the cable sets during implantation of the unit, the terminal fittings are preferably coded or differ in shape and/or size. Another possibility consists in providing one of the two cable sets, for example, the cable which leads to an actuator, with a terminal fitting according to FIG. 1, while for the other cable set, for example, the cable which leads to a sensor, there is a terminal fitting according to FIG. 3. It goes without saying that the front side of housing 10 is then provided accordingly with molding 26 and elastic body 32 for the respective terminal fittings.

Regardless of whether the front side of the housing is provided with rigid and/or elastic bodies, the end cap can also be connected permanently to one or more terminal fittings and cables. Since, in this case however, replacement, for example, of only one of the cable sets would not be not possible, this embodiment is less preferred.

Figure 4:
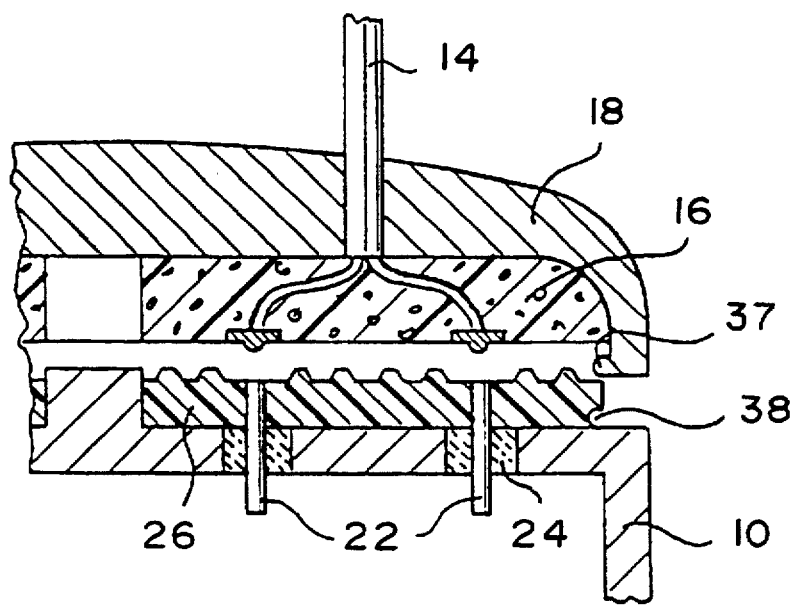
FIG. 4 shows a view similar to FIG. 3 of a modified version of the housing shown in FIG. 1.

FIG. 4 shows, in a section similar to that of FIG. 3, a further modified embodiment of the implantable unit in which engagement between the housing and sealing cap takes place via a catch connection instead of via a screw connection. For this reason, end cap 18 has one or more catch projections 37 on the inside of the edge thereof which faces housing 10. Projections 37 fit into housing recesses 38 when the housing and end cap are joined. In the embodiment shown in FIG. 4, recess 38 is formed by a projecting edge of the molding 26 which is attached to the side of the housing that contains feedthroughs 22. It goes without saying that a functionally analogous catch connection between the end cap and the housing 10 can be achieved independent of the shape of molding 26 by a corresponding configuration of end cap 18 and housing 10 themselves.

In order to be able to vary contact force $F_K$ and sealing force $F_D$, also when using a catch connection, one or more further recesses can be provided parallel to the recess 38 at varying heights. Alternatively, the component which is engaged by the catch projection 37 can have a sawtoothed surface allowing the height at which projection 37 is held relative to the housing 10 to be varied.

Figure 6:
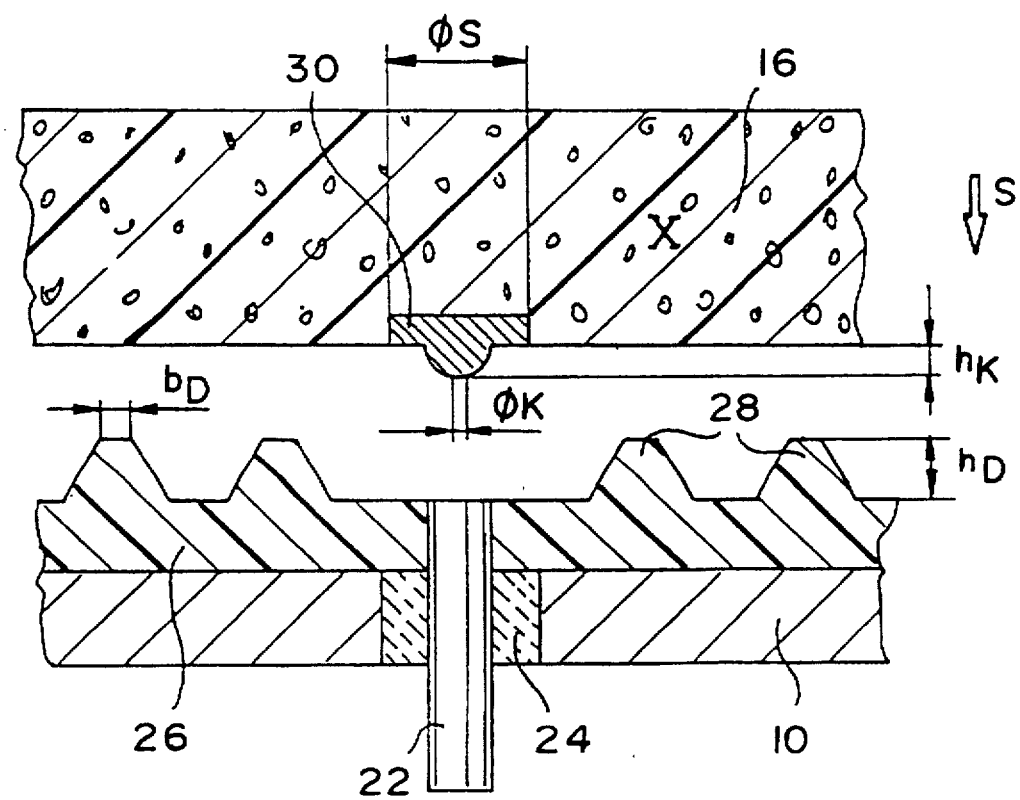
FIG. 6 shows a sectional view of the FIG. 5 contact arrangement in the opened state.

The following underlying functional parameters of the connection principle are shown in FIGS. 5 and 6:

diameter of the gas-tight point of contact $\emptyset_K$

Diameter $\emptyset_K$ must be selected to be so large that current carrying capacity is ensured for the selected metallic material.

diameter of the elastically supported contact $\emptyset_S$

Diameter $\emptyset_S$ must be selected to be so large that the elastic, electrically insulating material which is preferably made of silicone is not damaged and is not stressed beyond its elastic limit when the resilient restoration force is generated.

deformation path s

When the terminal fitting abuts the body located on the front side of the housing, the sealing lands are pressed by the closure mechanism into the molding by the length of deformation path s. The resulting restoration force produces sealing force $F_D$ and contact force $F_K$. Shore hardness X and the elastic limit of the elastic material play a role in this case.

Shore hardness X

The higher the Shore hardness of the elastic material, the higher the reset force for a given deformation path.

Projecting height of the contact $h_K$

The force produced with the closure mechanism generates both the pressure on the sealing lands and also on the points of contact. If the projecting height of the contact $h_K$ and the height of sealing lands $h_D$ are selected to be the same, the pressure is distributed proportionally to the respective surfaces and is produced by the spring action of the elastic material under deformation path s. If the projecting height of the contact $h_K$ is selected to be different than the height of sealing land $h_D$, the entire deformation path s takes effect only for one of the two contacts. In this way, the pressure to be produced on the point of contact and the pressure to be produced on the sealing lands can be adjusted independently of their surface ratios.

height of sealing lands $h_D$

The aforementioned relation to the projecting height of the contact applies. The required height of the sealing land depends on the overall geometry of the sealing lands, the elastic material, and its Shore hardness. If maximum pressure on the sealing lands is to prevail, the elastic material should not be pressed against the molding between the sealing lands. The height must be selected accordingly and corresponds at most to deformation path s.

width of sealing lands $b_D$

The narrower the sealing lands which are selected, the higher the pressure, but the elastic material should not be damaged.

For a current carrying capacity in the mA range, the amount of space required by the contact arrangements as compared to the aforementioned standardized cardiac pacemaker plug-and-socket connections can be significantly minimized.

The closing mechanism must press the terminal fittings against the housing with a defined closing force, so that a gas-tight contact closure is formed and the sealing effect is ensured. Before the force acts on the elastic material which produces a spring-like restoration force via deformation path s, the terminal fittings must be in the exactly correct position. One simple solution is to insert the terminal fittings into the end cap which is drawn against the housing using a screw with defined torque. This process is, however, only conditionally possible if the housing is already anchored in the bone bed since sealing takes place from the front.

To be able to operate the closing mechanism from overhead, in the modified embodiment illustrated in FIGS. 7 and 8, housing 40 has a type of trough 42 on its front end into which terminal fittings 44 are inserted from above. These terminal fittings are moved into the exact position using cover 46, which is mounted in the area of trough 42, and then are pressed against housing 40 by inserting a wedge 48 for a defined deformation distance. The peripheral out line of the terminal fittings 44 and the corresponding accommodation in trough 42 can be made in the aforementioned manner such that no terminal fitting fits into the receiver of another. Furthermore, FIG. 7 shows terminal fitting 44 which is designed for a four-pole connection.

According to FIG. 8, after inserting terminal fittings 44 into trough 42, cover 46 is mounted. By means of opening 50 in the cover 46, wedge 48 is placed between terminal fittings 44 and the side of wall 51 of trough 42 which is remote from housing 40, so that terminal fittings 44 are pushed by the defined deformation distance in the direction toward wall housing surface 54 having the contacts, and are pressed against this surface. In this case, wedge 48 can be placed and fixed using a screw 52, or a catch mechanism (not shown) can be provided by means of which manually inserted wedge 48 is fixed in the installation position.

The above described connection principle between a device to be implanted and actuator and/or sensor components allows an insulation impedance between the individual contacts of more than 50 MΩ, this value exceeding the insulation impedance of 50 kΩ required by the aforementioned DIN standard for cardiac pacemakers by several-fold. For example, in an implantable hearing aid, gains of >80 dB between the sensor and actuator are necessary without feedback occurring between the sensor signals and the actuator signals, and it should be possible to transmit analog signals in the microvolt range without distortion via the contact arrangement. The proposed implantable unit, thus, makes it possible to satisfy the high demands which apply to contact-making for implantable hearing aids and which correspond to the requirements of signal transmission in the audio and HiFi range.

In spite of a high degree of possible miniaturization, closing of the contact arrangements takes place easily, reliably and safely. Without using the typical male and female design of contacts in the form of a pin and receiving socket, there is no danger, in the proposed system, that the contacts can be broken, bent or otherwise damaged.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

We claim:

1. Implantable unit comprising a housing, at least one cable set and at least one contact arrangement for electrical connection of an electrical or electronic device which is hermetically sealed within the housing to said at least one cable set routed out of the housing; wherein the contact arrangement has a first contact, second contact supported on an elastic body, and a closing mechanism for engaging a front of the first contact with a front of the second contact and at least one sealing bridge which surrounds the first contact, and which is pressed into the elastic body when the contacts are engaged, said at least one sealing bridge sealing the contacts relative to the exterior of the unit.

2. Implantable unit according to claim 1, wherein said at least one sealing land comprises a plurality of concentric sealing lands.

3. Implantable unit according to claim 1, wherein said at least one contact arrangement comprises a plurality of contact arrangements; and wherein at least one sealing land is provided for each contact arrangement.

4. Implantable unit according to claim 1, wherein the first contact is fixed to the housing and is joined to the electrical or electronic device; and wherein the second contact is connected to the cable set.

5. Implantable unit according to claim 4, wherein the first contact is formed directly by a housing feedthrough of the electrical or electronic device; and wherein an electrically insulating molding surrounds the housing feedthrough.

6. Implantable unit according to claim 1, wherein the second contact is mounted to the housing and is connected to the electrical or electronic device in the housing; and wherein the first contact is connected to the at least one cable set.

7. Implantable unit according to claim 1, wherein the closing mechanism comprises a sealing cap which is connected to the at least one cable set and in which at least one of said first and second contacts is located, and an engagement arrangement for connecting the sealing cap to the housing.

8. Implantable unit according to claim 7, wherein the engagement arrangement has at least one threaded receptacle on the housing and at least one screw on the sealing cap.

9. Implantable unit according to claim 7, wherein the engagement arrangement has a catch connection which acts between the sealing cap and the housing.

10. Implantable unit according to claim 1, wherein a terminal fitting is provided on said at least one cable set and which terminal fitting carries at least one of said first and second contacts; wherein the closing mechanism has a sealing cap with a receiver for the at least one terminal fitting; and wherein an engagement arrangement is provided for connecting the sealing cap to the housing.

11. Implantable unit according to claim 10, wherein the engagement arrangement has at least one threaded receptacle on the housing and at least one screw on the sealing cap.

12. Implantable unit according to claim 10, wherein the engagement arrangement has a catch connection which acts between the sealing cap and the housing.

13. Implantable unit according to claim 1, wherein a terminal fitting is provided on said at least one cable set; wherein the housing has a trough-shaped receiver holding at least one terminal fitting at an end thereof; and wherein a wedge member is inserted between a side wall of the trough-shaped receiver which faces said end of the housing and the terminal fitting.

14. Implantable unit according to 13, wherein at least one screw is provided for adjusting and fixing the position of said wedge and for adjusting the force of the engagement between the first and second contacts.

15. Implantable unit according to claim 1, wherein the elastic body is made of silicone.

16. Implantable unit according to claim 1, wherein one of the first and second contacts has a rounded engagement surface.

17. Implantable unit according to claim 16, wherein the other of said first and second contacts has a generally flat surface which is engaged by said rounded engagement surface.

* * * * *